(12) United States Patent
Gu et al.

(10) Patent No.: US 9,314,173 B2
(45) Date of Patent: Apr. 19, 2016

(54) REMOTE CONTROLLER AND DISPLAY SYSTEM

(75) Inventors: Ren-Hau Gu, Hsin-Chu (TW);
Ming-Tsan Kao, Hsin-Chu (TW);
Sen-Huang Huang, Hsin-Chu (TW)

(73) Assignee: PIXART IMAGING INC., Hsin-Chu County (TW)

( * ) Notice: Subject to any disclaimer, the term of this patent is extended or adjusted under 35 U.S.C. 154(b) by 742 days.

(21) Appl. No.: 13/617,259

(22) Filed: Sep. 14, 2012

(65) Prior Publication Data
US 2013/0131474 A1  May 23, 2013

(30) Foreign Application Priority Data

Nov. 22, 2011   (TW) .............................. 100142661 A

(51) Int. Cl.
| | | |
|---|---|---|
| A61B 5/1455 | (2006.01) | |
| A61B 5/0205 | (2006.01) | |
| G06F 3/033 | (2013.01) | |
| A61B 5/024 | (2006.01) | |
| A61B 5/00 | (2006.01) | |
| G06F 3/03 | (2006.01) | |
| G06F 3/0354 | (2013.01) | |

(52) U.S. Cl.
CPC ........... A61B 5/02416 (2013.01); A61B 5/0205 (2013.01); A61B 5/6897 (2013.01); G06F 3/0304 (2013.01); G06F 3/0354 (2013.01); A61B 5/14551 (2013.01); G08C 2201/00 (2013.01)

(58) Field of Classification Search
CPC ............... A61B 5/6886; A61B 5/6826; A61B 5/14552; A61B 5/7203; A61B 5/0205; A61B 5/7214; A61B 5/02433; A61B 1/14551; A61B 5/7207; A61B 5/02416
See application file for complete search history.

(56) References Cited

U.S. PATENT DOCUMENTS

| | | | | |
|---|---|---|---|---|
| 5,983,120 A | * | 11/1999 | Groner et al. ................. | 600/310 |
| 5,990,866 A | * | 11/1999 | Yollin ........................... | 345/157 |
| 7,072,701 B2 | | 7/2006 | Chen et al. | |
| 7,697,966 B2 | * | 4/2010 | Monfre et al. ................ | 600/310 |
| 2003/0126593 A1 | * | 7/2003 | Mault ............................ | 725/10 |
| 2010/0305418 A1 | * | 12/2010 | Deliwala ............ | A61B 5/14551 |
| | | | | 600/324 |

FOREIGN PATENT DOCUMENTS

| | | |
|---|---|---|
| CN | 101317756 A | 12/2008 |
| CN | 201569991 U | 9/2010 |

* cited by examiner

*Primary Examiner* — Eric Winakur
(74) *Attorney, Agent, or Firm* — Hauptman Ham, LLP

(57) ABSTRACT

There is provided a remote controller including a plurality of press buttons, an optical finger mouse and a transmission interface. The press buttons are configured to trigger a control signal. The optical finger mouse is configured to detect a physiological characteristic and a displacement. The transmission interface is configured to output the control signal, the physiological characteristic and the displacement to a display device. There is further provided a display system.

20 Claims, 5 Drawing Sheets

REMOTE CONTROLLER AND DISPLAY SYSTEM

CROSS REFERENCE TO RELATED APPLICATION

This application claims the priority benefit of Taiwan Patent Application Serial Number 100142661, filed on Nov. 22, 2011, the full disclosure of which is incorporated herein by reference.

BACKGROUND

1. Field of the Disclosure

This disclosure generally relates to a human interface system and, more particularly, to a remote controller and a display system that have the function of detecting physiological characteristics of a user.

2. Description of the Related Art

As the optical finger mouse has a relatively small size, it is suitable for being applied to portable electronic devices. A conventional optical finger mouse can be used to detect an intensity variation of reflected light from a finger surface of a user so as to accordingly identify a finger contact status and a finger displacement with respect to a touch surface. However, with the development of industry, users spend more and more time on utilizing various portable electronic devices that puts a lot of stress on their bodies. Therefore, if a portable electronic device also has the function of detecting physiological characteristics of a user and is able to give a warning when necessary, the overuse of the portable electronic devices can then be avoided.

Conventional pulse oximeters utilize a noninvasive method to monitor the blood oxygenation and the heart rate of a user. A conventional pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 and entitled "Method for spectrophotometric blood oxygenation monitoring". After the intensity variation of the penetrating light of the two wavelengths is detected, the blood oxygenation can be calculated according to equation (1):

$$\text{Oxygen saturation} = 100\% \times [HbO_2]/([HbO_2]+[Hb]) \quad (1)$$

wherein $[HbO_2]$ is an oxyhemoglobin concentration; and $[Hb]$ is a deoxy-hemoglobin concentration.

Generally, the intensity variation of the penetrating light of the two wavelengths detected by a pulse oximeter is similar to FIG. 1. This is because blood vessels will expand and contract with heartbeats such that the blood volume that the light beams pass through will change to accordingly change the ratio of light energy being absorbed. Therefore, the absorptivity of blood of different light spectra can be calculated according to the intensity information changing continuously so as to calculate the physiology information, e.g. the oxyhemoglobin and deoxyhemoglobin concentration, respectively. Finally, the blood oxygenation can be calculated according to equation (1).

However, as conventional pulse oximeters detect the intensity variation of the penetrating light, different intensity signals will be detected by detecting different parts of the human body. In addition, when the part of the human body being detected has a movement, a disturbed signal can be detected such that it is not possible to calculate correct physiology information. Therefore, conventional pulse oximeters cannot be applied to electronic devices operated in a moving state.

Accordingly, the present disclosure provides a remote controller and a display system capable of detecting physiological characteristics of a user, wherein the signal noise caused by the finger movement can be eliminated by the remote controller in detecting the physiological characteristics.

SUMMARY

It is an object of the present disclosure to provide a remote controller and a display system in which the remote controller may detect a finger displacement, a finger contact status and a physiological characteristic of a user by analyzing reflected light from a finger, and generate a control signal according to an operating state of at least one press button to accordingly control a display device to perform a corresponding operation.

It is another object of the present disclosure to provide a remote controller chip that may detect a finger displacement, a finger contact status and a physiological characteristic of a user by analyzing reflected light from a finger, and generate a control signal according to an operating state of at least one press button so as to output encoded, sequenced and/or compressed finger information, physiology information and control signal information.

It is another object of the present disclosure to provide a remote controller and a display system that may detect a finger displacement, a finger contact status and a physiological characteristic of a user, and has a mechanism of eliminating the interference from ambient light sources.

It is another object of the present disclosure to provide a remote controller and a display system that may detect a finger displacement, a finger contact status and a physiological characteristic of a user, and has the denoising mechanism.

It is another object of the present disclosure to provide a remote controller and a display system that may detect a finger displacement, a finger contact status and a physiological characteristic of a user, and may enter a sleep mode after idling for a predetermined time period.

It is another object of the present disclosure to provide a remote controller and a display system that may detect a finger displacement, a finger contact status and a physiological characteristic of a user, and the physiological characteristic may be abandoned if the finger displacement is too large.

The present disclosure provides a remote controller configured to detect and output a physiological characteristic of a finger and a control signal. The remote controller includes a plurality of press buttons, a first light source, a second light source, a light control unit, at least one image sensor and a processing unit. The press buttons are configured to trigger the control signal. The first light source provides light of a first wavelength to the finger. The second light source provides light of a second wavelength to the finger. The light control unit is configured to control on-states of the first light source and the second light source. The image sensor receives reflected light from the finger at a sampling frequency to generate a plurality of first image frames corresponding to the on-states of the first light source and a plurality of second image frames corresponding to the on-states of the second light source. The processing unit is configured to calculate the physiological characteristic according to the first image frames and the second image frames, and to generate the control signal according to an operating state of the press buttons.

The present disclosure further provides a remote controller for being operated by a user. The remote controller includes a plurality of press buttons, an optical finger mouse and a transmission interface. The press buttons are configured to trigger a control signal. The optical finger mouse is configured to detect a physiological characteristic of the user and a finger displacement. The transmission interface is configured to output the control signal, the physiological characteristic and the finger displacement.

The present disclosure further provides a display system includes a display device and a remote controller. The display device is configured to display images. The remote controller is configured to output a control signal and a physiological characteristic to the display device so as to control the display device to update the images being displayed according to the control signal and to display the physiological characteristic.

In the embodiments of the present disclosure, each of the first image frames is divided into at least two parts and an average brightness of each part is calculated; and the average brightness of the each part of the first image frames is calculated to obtain a first intensity variation using independent component analysis or blind source separation. Each of the second image frames is divided into at least two parts and an average brightness of each part is calculated; and the average brightness of the each part of the second image frames is calculated to obtain a second intensity variation using independent component analysis or blind source separation. The physiological characteristic is calculated according to the first intensity variation and the second intensity variation.

In the remote controller and the display system of the present disclosure, the physiological characteristic may include a blood oxygenation and a heart rate. In the present disclosure, the movement informant and the physiology information are separated by means of independent component analysis (ICA) or blind source separation (BSS) so as to effectively eliminate the signal noise caused by the finger movement.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 2A:
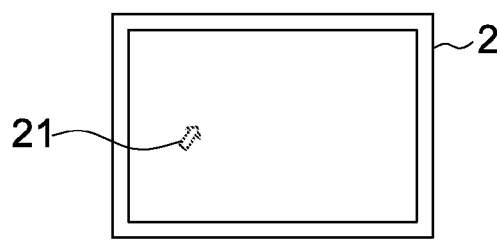
FIG. 2A shows a schematic diagram of the display system according to an embodiment of the present disclosure.
Figure 2A:
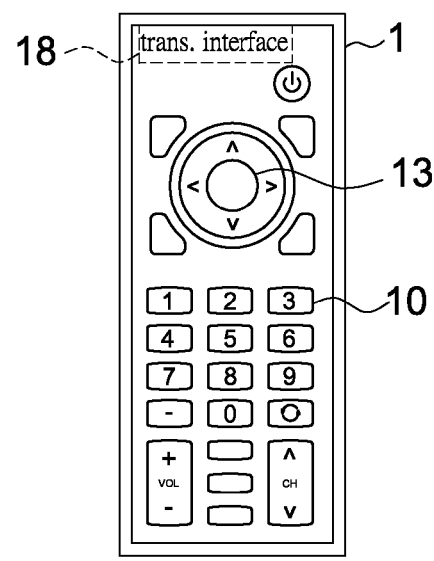

Please refer to FIG. 2A, it shows a schematic diagram of the display system according to an embodiment of the present disclosure. The display system includes a remote controller 1 and a display device 2. The display device 2 may be a television, a projection screen, a game machine screen, a computer screen or other display devices for displaying images. Associated with the display device 2, the remote controller 1 may be a television controller, a projection screen controller, a game machine controller, a computer controller or the like and is configured to control the display device 2 to update images being displayed or display a physiological characteristic, wherein the remote controller 1 may be wired or wirelessly coupled to the display device 2. The remote controller 1 is configured to detect and output a physiological characteristic, a contact status, a finger displacement and a control signal to the display device 2.

The remote controller 1 includes a plurality of press buttons 10, an optical finger mouse and a transmission interface 18, wherein the optical finger mouse includes a touch member 13 for a finger to operate thereon, and the touch member 13 may be combined with one of the press buttons 10 or separated from the press buttons 10. The press buttons 10 are configured to trigger a control signal according to a pressing state of a user, e.g. generating the control signal associated with different resistances, voltage values or oscillation frequencies by pressing at least one press button. The optical finger mouse is configured to detect a contact status of the finger of a user, a displacement and a physiological characteristic of the user, wherein the physiological characteristic may include a blood oxygenation and a heart rate. In this embodiment, the optical finger mouse starts to detect the displacement and the physiological characteristic when identifying that the contact status is a touch state (i.e. the finger 9 touches the optical finger mouse). The transmission interface 18 is configured to wired or wirelessly transmit the control signal, contact status, displacement and physiological characteristic to the display device 2 such that the display device 2 may update images being displayed according to the control signal and display the displacement and physiological characteristic. It is appreciated that although the touch member 13 is disposed on an upper surface of the remote controller 1, in other embodiments the touch member 13 may be disposed on a bottom surface of the remote controller 1 or other positions that are easily touched by the finger.

Figure 2B:
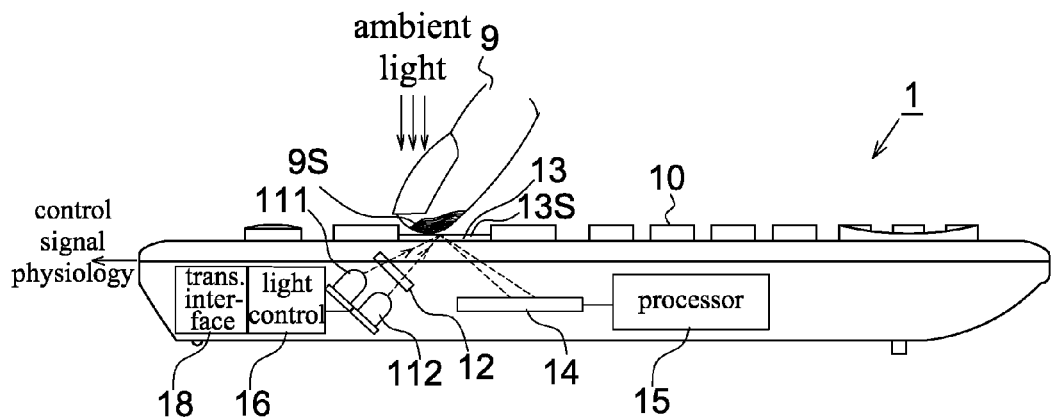
FIG. 2B shows a schematic diagram of the remote controller according to an embodiment of the present disclosure.

Please refer to FIG. 2B, it shows a schematic diagram of the remote controller 1 according to an embodiment of the present disclosure. The remote controller 1 includes a plurality of press buttons 10, two light sources 111-112, a light guide 12 (a number of the light guide herein is only exemplary), a touch member 13, an image sensor 14, a processing unit 15, a light control unit 16 and a transmission interface 18. It should be mentioned that the spatial relationship between every component in FIG. 2B is only exemplary and not to limit the present disclosure. The press buttons 10 may have functions of, but not limited to, channel selection, parameter adjustment and device selection, and is configured to trigger a control signal according to an operating state (e.g. the pressing state) of a finger 9. The light sources 111-112 may be light emitting diodes or laser diodes and are configured to respectively emit light of different wavelengths to the finger surface 9S. Preferably, said different wavelengths are the two wavelengths used in conventional pulse oximeters, e.g. red light of wavelength about 660 nm and infrared light of wavelength about 905, 910 or 940 nm. It is appreciated that the wavelengths mentioned herein are the center wavelength of respective illumination spectrum of the light sources 111-112.

The light guide 12 is configured to direct the light emitted by the light sources 111 and 112 to the touch member 13, wherein the structure, number and light guiding mechanism of the light guide 12 do not have any limitation as long as the light guide 12 is able to direct light to the touch member 13. In other embodiments, if the light emitted from the light sources 111-112 can directly impinge on the touch member 13, the light guide 12 may not be implemented.

The touch member 13 has a touch surface 13S for the finger 9 to operate thereon, and the touch member 13 is preferably transparent to the light emitted by the light sources 111 and 112 such that when the finger 9 approaches or touches the touch surface 13S of the touch member 13, the light emitted by the light sources 111 and 112 is reflected. It is appreciated that an area of the touch surface 13S may be larger or smaller than that of the finger surface 9S.

The image sensor 14 receives, with a sampling parameter, reflected light from the touch member 13 (more specifically from the finger surface 9S) to generate a plurality of image frames, which may have a size of 16×16, wherein the sampling parameter may include an exposure time and an image gain, e.g. an analog gain or a digital gain, but not limited thereto. The image sensor 14 is preferably an active matrix sensor, e.g. a CMOS image sensor.

The processing unit 15 generates a control signal corresponding to an operating state of the press buttons 10, and detects a contact status and a displacement of the finger 9 with respect to the touch surface 13S and a physiological characteristic of the user according to a plurality of image frames outputted by the image sensor 14. The control signal, contact status, displacement and physiological characteristic obtained by the processing unit 15 may be wired or wirelessly sent to a display device having at least one response unit for displaying or corresponding control, wherein the response unit may be a display device, a lamp device, a seven-segment display and/or a sound device. The display device may be a portable electronic device or a home appliance.

The light control unit 16 is coupled to the processing unit 15 and configured to control on-states and off-states of the light sources 111-112 corresponding to the image capturing of the image sensor 14, and details thereof will be described hereinafter.

The transmission interface 18 wired or wirelessly transmits the control signal, contact status, displacement and physiological characteristic to the display device 2.

In this embodiment, the light sources 111 and 112, the image sensor 14, the processing unit 15 and the light control unit 16 are served as an optical finger mouse configured to detect a contact status, a displacement and a physiological characteristic of the finger 9.

Figure 2C:
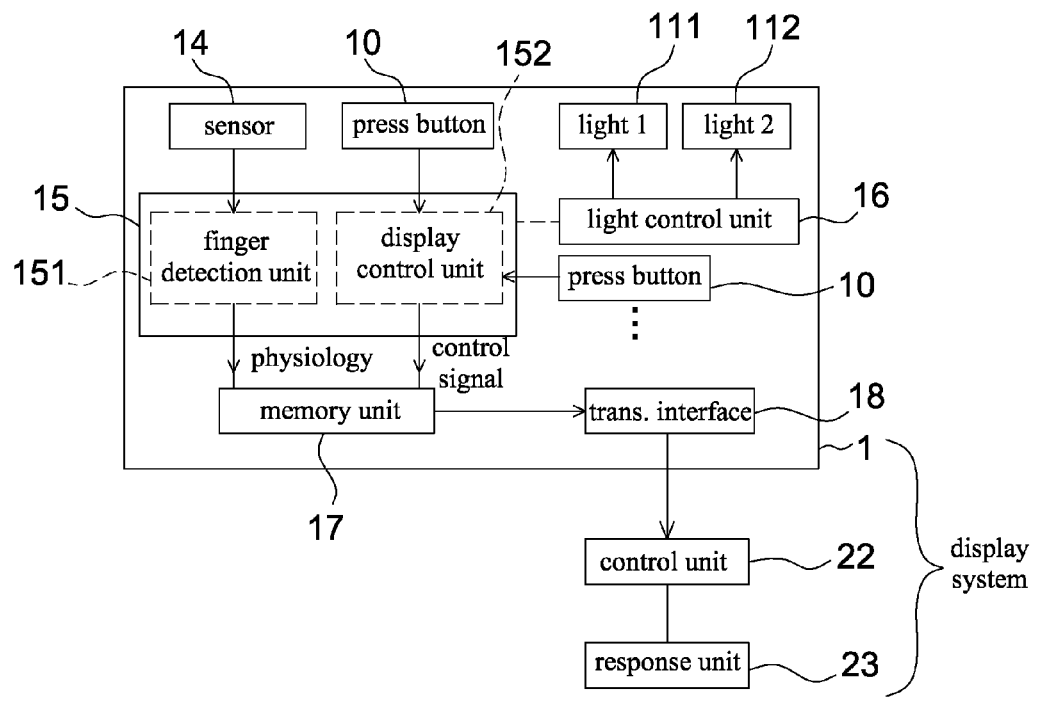
FIG. 2C shows a schematic block diagram of the remote controller according to an embodiment of the present disclosure.

Please refer to FIGS. 2A to 2C, FIG. 2C shows a schematic block diagram of the remote controller 1 according to an embodiment of the present disclosure. The remote controller 1 includes a plurality of press buttons 10, a first light source 111, a second light source 112, the image sensor 14, the processing unit 15, the light control unit 16, a memory unit 17 and the transmission interface 18, wherein the remote controller 1 and a control unit 22 and a response unit 23 may be combined as a display system. Because the processing unit 15 has multifunction, the processing unit 15 may further include a finger detection unit 151 configured to detect the contact status, finger displacement and physiological characteristic of the finger 9 with respect to the touch surface 13S and a display control unit 152 configured to generate and output the control signal according to the operating state (e.g. the pressing state) of the press buttons 10. That is, the processing unit 15 may be a single element or composed of two elements.

The first light source 111 may emit red light of wavelength about 660 nm to the finger 9, and the second light source 112 may emit infrared light of wavelength about 905, 910 or 940 nm to the finger 9. Broadly speaking, the first light source 111 and the second light source 112 respectively emit light of the two wavelengths used in conventional pulse oximeters. The light control unit 16 controls the first light source 111 and the second light source 112 to emit light. The image sensor 14 receives reflected light associated with the first light source 111 and the second light source 112 from the finger surface 9S. The memory unit 17 is configured to store the control signal, contact status, displacement and physiological characteristic obtained by the processing unit 15 and to store various parameters needed in the calculation, wherein the control signal may not be stored in the memory unit 17 and is transmitted through the transmission unit 18. The transmission interface 18 is configured to wired or wirelessly transmit the control signal, contact status, displacement and physiological characteristic stored in the memory unit 17 to an external control unit 22, wherein the wired and wireless communication techniques are well known and thus details thereof are not described herein. The control unit 22 may be integrated in the display device 2 having at least one response unit 23 and is configured to control the display device 2 to display and/or respond the received control signal, contact status, displacement and physiological characteristic via the response unit 23.

The remote controller 1 of the present disclosure may incorporate with a display device 2 having a response unit 23 such that a user may control a cursor shown on the response unit 23 or a software executed by the display device 2 using the remote controller 1, and the response unit 23 may give a warning when the physiological characteristic indicates that the user is in a fatigue or excitatory state (e.g. according to a value of the physiological characteristic), wherein the method of showing the physiological characteristic and the warning may be implemented by, for example, showing on a screen, representing by a lamp device or by sound controlled a software. The display device 2 may switch screens, update images, adjust volume, adjust display parameters according to the control signal; may control the motion of a cursor according to the displacement; may show the physiological characteristic and generate a warning state when the physiological characteristic exceeds a predetermined value, such as reducing the darkness of the screen, inserting an image object, playing a sound and so on.

In one embodiment, the remote controller 1 may include two image sensors configured to detect light of two different wavelengths respectively emitted by the light sources 111 and 112 (i.e. the image sensor 14 is replaced by two image sensors), wherein an optical bandpass filter may be integrated on one or two of the image sensors in order to select the desired spectrum.

As the method of generating the control signal by the processing unit 15 according to the press buttons 10 are well known, details thereof are not described herein. Only the methods of calculating the contact status, finger displacement and physiological characteristic by the processing unit 15 will be described hereinafter; that is, only the operation of the optical finger mouse formed by the light sources 111 and 112, the image sensor 14, the processing unit 15 (or the finger detection unit 151) and the light control unit 16 will be described hereinafter.

Sampling Mechanism

The optical finger mouse of the present disclosure utilizes two light sources 111 and 112 and may perform two functions simultaneously, wherein the function of detecting the contact status and displacement may use the image frames associated with any wavelength without limitation, but the function of detecting the physiological characteristic needs to be respectively performed corresponding to the image frames of different wavelengths. First, the sampling mechanism of the image frames in the present disclosure is illustrated hereinafter.

Figure 3:
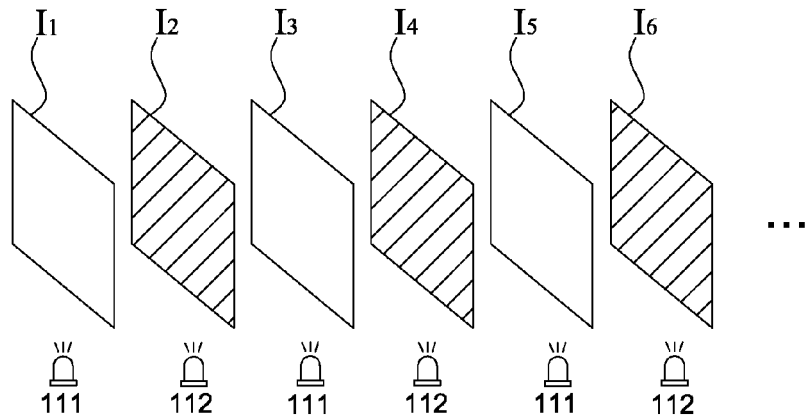
FIG. 3 shows a schematic diagram of the image frames captured by the image sensor of the remote controller according to the embodiment of the present disclosure.

In one embodiment, the light control unit 16 controls the first light source 111 and the second light source 112 to turn on alternatively. The image sensor 14 captures image frames at a high and fixed sampling frequency (e.g. 3,000 frames/sec) and synchronizing to the turning on (i.e. on-states) of the first light source 111 or the second light source 112, and outputs a plurality of image frames $I_1$ to $I_6$ ... as shown in FIG. 3 to the processing unit 15 (or the finger detection unit 151), wherein the image frames $I_1$ to $I_6$ ... include first image frames $I_1$, $I_3$, $I_5$ ... corresponding to the on-states of the first light source 111 and second image frames $I_2$, $I_4$, $I_6$ ... corresponding to the on-states of the second light source 112.

The processing unit 15 may identify a contact status and calculate a displacement according to the first and second image frames $I_1$ to $I_6$ ..., e.g. identifying whether the finger 9 approaches or touches the touch surface 13S according to a comparison result of comparing a brightness value of the first and second image frames with at least one brightness threshold, wherein when the brightness value of the image frames is larger or smaller than the brightness threshold, a touch state is entered. After entering the touch state, the processing unit 15 may calculate the displacement according to the correlation between two first image frames, between one first image frame and one second image frame, or between two second image frames. It should be mentioned that the identification of the contact status and the calculation of the displacement in the present disclosure need to use the image frames associated with the reflected light of two different wavelengths and thus are different from conventional navigation devices.

The processing unit 15 may calculate an intensity variation of first image frame according to the first image frames $I_1$, $I_3$, $I_5$ ..., and calculate an intensity variation of second image frame according to the second image frames $I_2$, $I_4$, $I_6$ ... (described later), and accordingly calculate the absorptivity of blood in two spectra so as to obtain [$HbO_2$] and [Hb]. Finally, the blood oxygenation may be calculated according to equation (1), and the heart rate may also be calculated according to a comparison result of comparing the intensity variation of first image frame and/or the intensity variation of second image frame with at least one pulse threshold.

Figure 4:
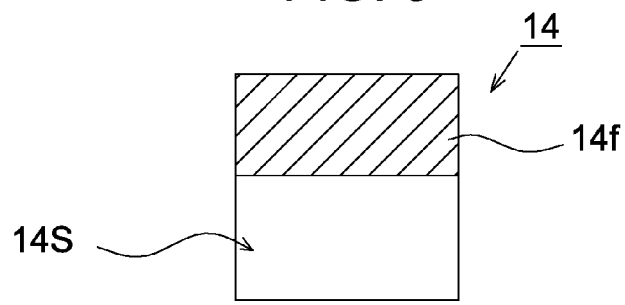
FIG. 4 shows a schematic diagram of the image sensor of the remote controller according to the embodiment of the present disclosure, wherein an optical filter is disposed in front of a part of a sensing surface thereof.

In another embodiment, the light control unit 16 controls the first light source 111 and the second light source 112 to turn on simultaneously and synchronizing to the image capturing of the image sensor 14; that is, the image sensor 14 may receive reflected light of two wavelengths simultaneously. Therefore, in this embodiment an optical filter 14f is further disposed in front of at least a part of a sensing surface 14S of the image sensor 14 as shown in FIG. 4, wherein the optical filter 14f may be an optical bandpass filter to allow the part of the sensing surface 14S behind the optical filter 14f to only receive the spectrum of light of the first light source 111 or the second light source 112 such that the processing unit 15 may distinguish the first image frame (i.e. the part of the image frame associated with the first light source 111) and the second image frame (i.e. the part of the image frame associated with the second light source 112). It is appreciated that in the present disclosure the position and the area of the optical filter 14f are not limited to those shown in FIG. 4.

In this manner, the processing unit 15 may also calculate a contact status and a displacement according to the first and second image frames $I_1$ to $I_6$ .... The processing unit 15 may also calculate the intensity variation of first image frame according to the first image frames $I_1$, $I_3$, $I_5$ ..., calculate the intensity variation of second image frame according to the second image frames $I_2$, $I_4$, $I_6$ ..., and calculate at least one of the blood oxygenation and the heart rate according to the two intensity variations.

It is appreciated that as the sensing efficiency of the image sensor 14 toward light of different wavelengths may be different or the illumination brightness values of the first light source 111 and the second light source 112 may not be exactly identical, the brightness value of the image frames captured by the image sensor 14 may be previously adjusted (e.g. by adjusting the sampling parameter, such as an exposure time and an image gain, of the image frames corresponding to different wavelengths) before the shipment of the remote controller 1 such that the image frames initially outputted by the image sensor 14 may have substantially identical brightness values to eliminate the possibility of error.

In this embodiment, the light control unit 16 controls the first light source 111 and the second light source 112 such that the image sensor 14 captures reflected light from the finger 9 at a sampling frequency to generate a plurality of first image frames corresponding to on-states of the first light source 111 and a plurality of second image frames corresponding to on-states of the second light source 112. The processing unit 15 calculates the contact status, finger displacement and physiological characteristic according to the first image frames and the second image frames.

Mechanism Of Eliminating Ambient Light Interference

In FIG. 2B, as the touch member 13 and the finger 9 are light transmissive, the ambient light outside the remote controller 1 can penetrate the finger 9 and the touch member 13 and then be received by the image sensor 14 to degrade the image quality of the image frames captured thereby. In the present disclosure, the light control unit 16 may control the first light source 111 and the second light source 112 to turn off (i.e. the off-state) in predetermined time intervals.

Figure 5:
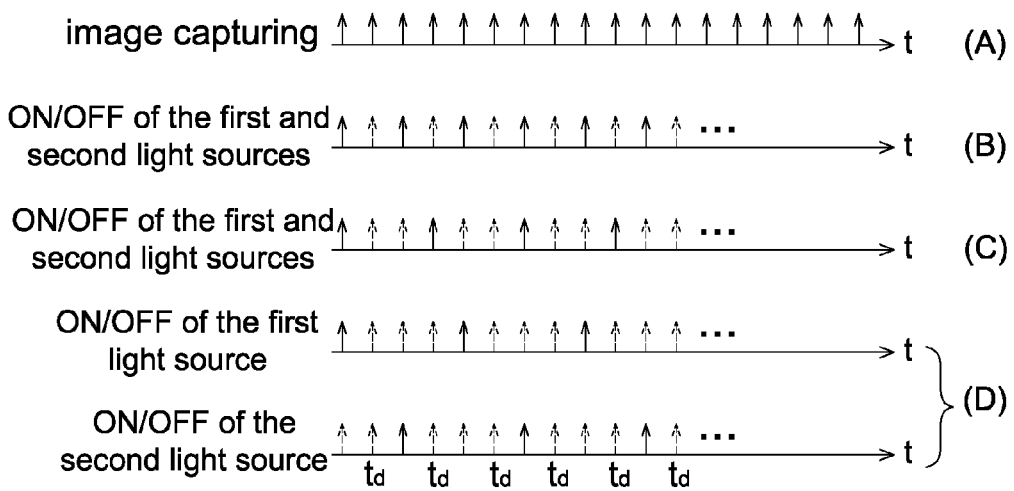
FIG. 5 shows a schematic diagram of the image capturing of the image sensor and the ON/OFF of the light source in the remote controller according to the embodiment of the present disclosure.

For example please refer to FIG. 5, it shows a schematic diagram of the image capturing of the image sensor 14 and the ON/OFF of the first light source 111 and the second light source 112, wherein in FIGS. 5(B)-5(D) solid arrows denote the on-states of the light sources (or the lighting at a first brightness value) and dashed arrows denote the off-states of the light sources (or the lighting at a second brightness value), wherein the second brightness value may be smaller than the first brightness value. FIG. 5(A) shows that the image sensor 14 captures image frames at a fixed sampling frequency. FIG. 5(B) shows that the first light source 111 and the second light source 112 are alternatively turned on and turned off at the same time, and thus the image sensor 14 may alternatively capture bright image frames (i.e. corresponding to the on-states or the first brightness value of the light sources) and dark image frames (i.e. corresponding to the off-states or the second brightness value of the light sources). FIG. 5(C)

shows that the first light source 111 and the second light source 112 are simultaneously turned on once after being turned off two image periods, and this case is generally for a lower displacement of the finger 9. As mentioned above, when the first light source 111 and the second light source 112 are turned on simultaneously, e.g. FIGS. 5(B) and 5(C), the image sensor 14 further includes an optical filter 14f (as shown in FIG. 4) for spatially distinguishing the image frame associated with different light sources such that one part of the image sensor 14 may sense reflected light associated with the first light source 111 and the other part thereof may sense reflected light associated with the second light source 112.

When the finger 9 touches or approaches the touch surface 13S, the bright image frames, which are associated with the on-states of the light sources, include components of (reflected light from finger+stray light+ambient light), and the dark image frames, which are associated with the off-states of the light sources, include only the component of (ambient light). Therefore, if a dark image frame is subtracted from a bright image frame, the interference from the ambient light can be effectively eliminated. The processing unit 15 may calculate the contact status, finger displacement and physiological characteristic according to differential images between the bright image frames and the dark image frames.

Please refer to FIG. 5(D), it shows an embodiment in which the first light source 111 and the second light source 112 are turned on alternatively. In this embodiment, in order to allow the image sensor 14 to be able to capture dark image frames, the light control unit 16 controls the first light source 111 and the second light source 112 to alternatively turn on every other image frame, e.g. the two light sources are both turned off at time $t_d$ in FIG. 5(D). Accordingly, the processing unit 15 may calculate a differential first image (i.e. bright first image frame-dark image frame) and a differential second image (i.e. bright second image frame-dark image frame), and calculate the contact status, finger displacement and physiological characteristic according to the differential first and second images. As mentioned above, if the first light source 111 and the second light source 112 are turned on alternatively, the image sensor 14 temporally distinguishes the image frames associated with different light sources.

In this embodiment, the light control unit 16 controls the first light source 111 and the second light source 112 to turn on simultaneously or alternatively and the image sensor 14 is able to capture dark image frames when both the light sources are turned off. The interference from ambient light is eliminated by calculating a difference between the bright image frame and the dark image frame. It is appreciated that the on-states and the off-states of each light source shown in FIG. 5 are only exemplary and not to limit the present disclosure.

Denoising Mechanism

As the image frames captured by the image senor 14 generally include noise which is randomly distributed in the image frames being captured. Therefore, in the present disclosure it is able to calculate a sum of M image frames to increase the signal-to-noise ratio (SNR) thereby improving the calculation accuracy of the physiological characteristic. For example, it is able to calculate a sum of 10 image frames and two groups of 10 image frames may have partially repeated image frames or totally different 10 image frames. It is appreciated that if the first light source 111 and the second light source 112 are turned on alternatively, the sum of image frames in this embodiment may be a sum of the first image frames (e.g. $I_1+I_3+I_5+\ldots$ as shown in FIG. 3) and a sum of the second image frames (e.g. $I_2+I_4+I_6+\ldots$ as shown in FIG. 3) since two intensity variations need to be calculated respectively. However, if the first light source 111 and the second light source 112 are turned on simultaneously, the sum of image frames in this embodiment is a sum of successive image frames (e.g. $I_1+I_2+I_3+I_4+I_5+I_6+\ldots$ as shown in FIG. 3), and the two intensity variations may be spatially distinguished by post-processing. In addition, if the mechanism of eliminating ambient light interference described above is incorporated in this embodiment, the sum of image frames in this embodiment is a sum of the differential images; that is, the process of eliminating ambient light interference is performed and then the process of denoising is performed successively. In other embodiments, only one of the mechanism of eliminating ambient light interference and the denoising mechanism is performed.

As mentioned above, the image sensor 14 may capture image frames with different sampling parameters at different conditions, e.g. the image sensor 14 may have different absorption of light at different wavelengths. Therefore different sampling parameters, such as different exposure times and different image gains, may be used to make the first image frames and the second image frames have substantially identical initial brightness values in order to correctly perform the post-processing on the image frames; that is, the sampling parameters associated with the first image frames and the second image frames may be different. In the present disclosure, in order to eliminate the influence of different sampling parameters, every image frame or the sum of M image frames or the average of M image frames may be normalized by the sampling parameter, e.g. (a sum of M image frames/sampling parameter) or (an average of M image frames/sampling parameter), wherein M is a positive integer.

Calculating Physiological Characteristics

Corresponding to the on-states of different light sources, the image frames captured by the image sensor 14 may contain physiology information and finger movement information at the same time. Therefore, in the present disclosure the processing unit 15 (or the finger detection unit 151) has to separate two types of information at first and then is able to calculate the physiological characteristic correctly. In the present disclosure, the processing unit 15 may separate the two types of information according to, for example, independent component analysis (ICA) or blind source separation (BSS).

Figure 1:
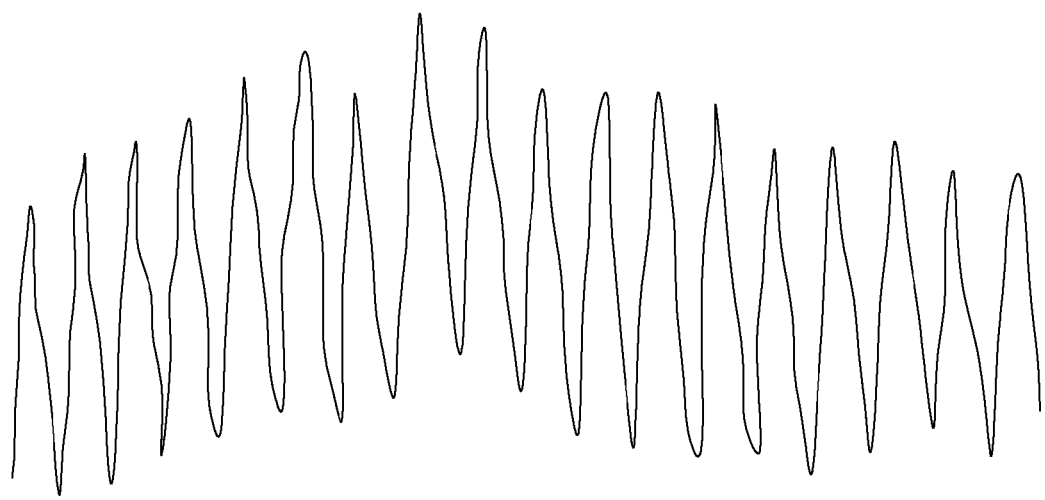
FIG. 1 shows a schematic diagram of an intensity variation of the penetrating light detected by pulse oximeters.
Figure 6:
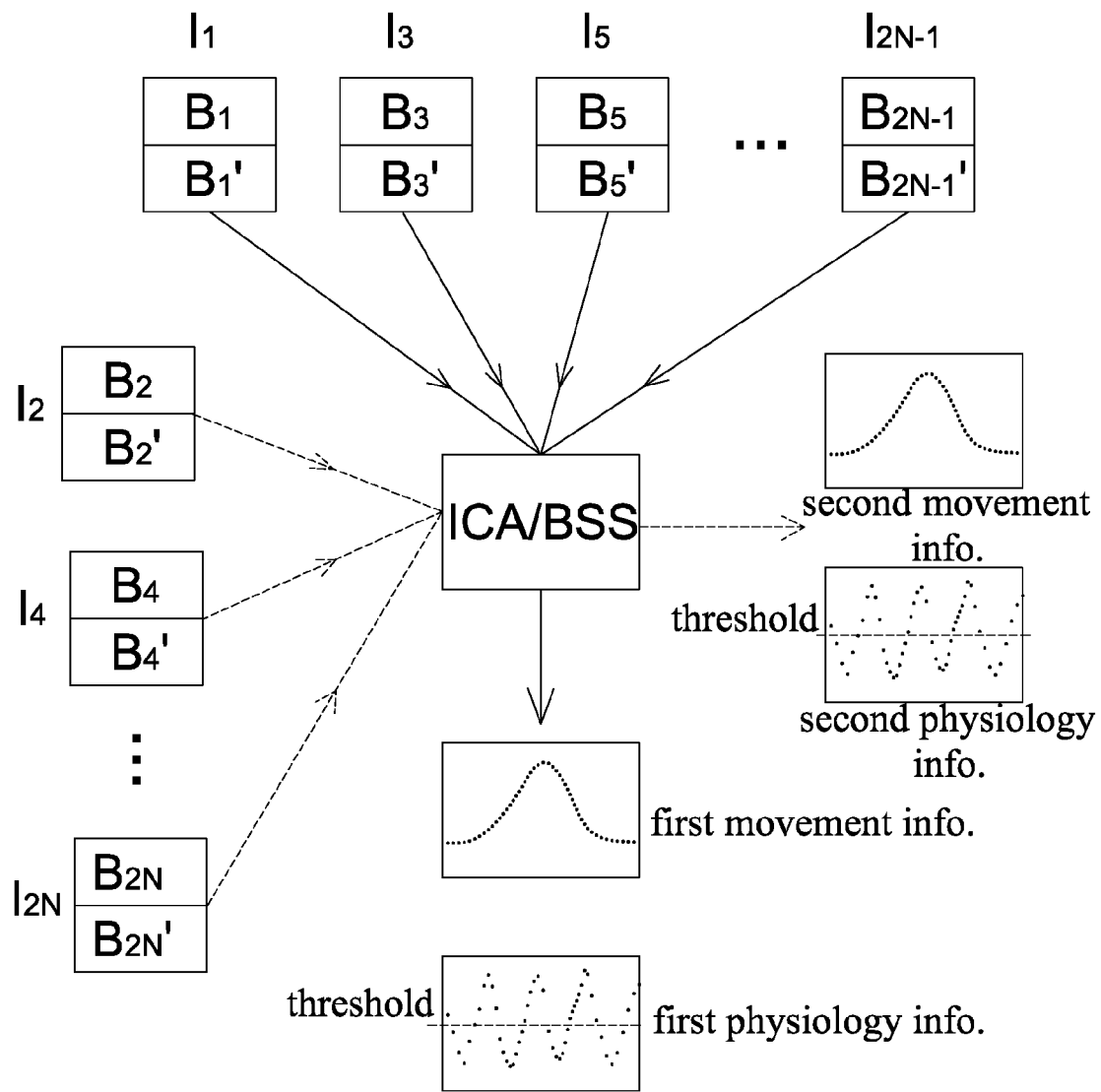
FIG. 6 shows a schematic diagram of separating the movement information and the physiology information by the processing unit of the remote controller according to the embodiment of the present disclosure.
Figure 7:
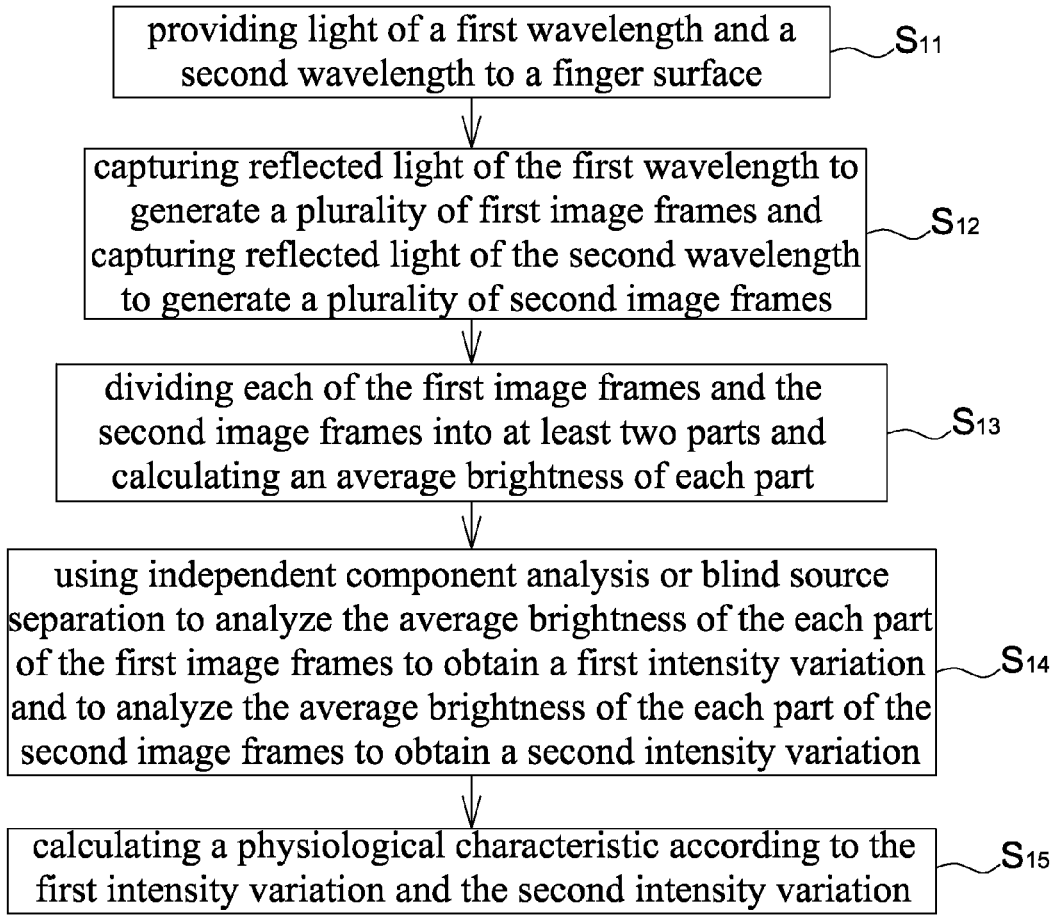
FIG. 7 shows a flow chart of the physiology detection method according to an embodiment of the present disclosure.

Please refer to FIGS. 3 and 6, taking the first image frames $I_1, I_3, I_5 \ldots$ shown in FIG. 3 as an example, each of the first image frames (e.g. original first image frames or the first image frames processed by the mechanism of eliminating ambient light interference and/or normalizing mechanism) or each of the sum of a plurality of first image frames (e.g. a sum of M original first image frames or a sum of M first image frames processed by the mechanism of eliminating ambient light interference and/or normalizing mechanism) is divided into at least two parts and an average brightness of each part is calculated, e.g. the image frame $I_1$ is divided into two parts respectively having an average brightness $B_1$ and $B_1'$; the image frame $I_3$ is divided into two parts respectively having an average brightness $B_3$ and $B_3'$; ...; the image frame $I_{2N-1}$ is divided into two parts respectively having an average brightness $B_{2N-1}$ and $B_{2N-1}'$, wherein the image frames may be divided into more than two parts in other embodiments. Next, a first movement informant and a first physiology information is separated from the divided image frames according to independent component analysis (ICA) or blind source separation (BSS) method as shown in FIG. 6, and each of the information is shown as a curve of intensity variation. In the present disclosure the movement information is abandoned and the physiological characteristic is calculated only according to the physiology information (i.e. the intensity variation of image frame). It is appreciated that as the sampling frequency of the image sensor 14 is much higher than the heart rate, the separated physiology information is shown as a curve of the intensity variation in accordance with the pulse beating (i.e. similar to FIG. 1), but the separated movement information is not limited to that shown in FIG. 6. In addition, the two parts divided from the image frames are not necessary to be the upper and the lower parts of the image frames. In addition, as it is necessary to respectively calculate the physiology information associated with two different wavelengths, the aforementioned separation process is performed respectively on the first image frames $I_1, I_3, I_5 \ldots$ (i.e. corresponding to the on-state of the first light source) and the second image frames $I_2, I_4, I_6 \ldots$ (i.e. corresponding to the on-state of the second light source) such that second movement information and second physiology information can be retrieved from the second image frames $I_2, I_4, I_6 \ldots$, wherein the second movement information is abandoned and the intensity variation of the second physiological information is kept. It should be mentioned that, if the information separation is performed on the sum or average of the image frames, each of $I_1$ to $I_{2N-1}$ and $I_2$ to $I_{2N}$ shown in FIG. 6 represents a sum or an average of M image frames or normalized results thereof.

It should be mentioned that the contact status and the displacement of the finger 9 are calculated by the processing unit 15 directly according to the original first image frames and second image frames without using the separated first and second movement information. The ICA and BSS methods are mainly configured to separate combined signals. When the separated movement information is abandoned, it is able to eliminate the signal noise caused by the finger movement.

In the present disclosure, the processing unit 15 further calculates a heart rate according to a comparison result of comparing at least one pulse threshold with a first intensity variation (i.e. the first physiology information) and/or a second intensity variation (i.e. the second physiology information).

Sleep Mode

The remote controller 1 of the present disclosure may enter a sleep mode after idling for a predetermined time period. For example, when the processing unit 15 identifies that a finger 9 does not approach or touch the touch surface 13S within the predetermined time period, the sleep mode is entered.

Mechanism of Removing Physiological Characteristic

Although the processing unit 15 of the remote controller 1 of the present disclosure may calculate the displacement and the physiological characteristic simultaneously, accurate physiological characteristics are preferably obtained when the displacement is relatively small. Therefore, in the present disclosure the processing unit 15 may previously identify whether the finger displacement is larger than a predetermined value (i.e. a displacement threshold). When the finger displacement is larger than the predetermined value, the image frames captured by the image sensor 14 are only used to calculate the displacement or to identify the contact status but not used to calculate the physiological characteristic; or even though the physiological characteristic is calculated, the physiological characteristic is directly removed from the memory unit 17 without being sent by the transmission interface 18. The predetermined value may be determined according to different applications, e.g. according the size of the sensing surface 13S and/or the searching block, but not limited thereto.

The physiology detection method of the remote controller 1 according to reflected light from the finger surface 9S includes the steps of: providing light of a first wavelength and a second wavelength to a finger surface (Step $S_{11}$); capturing reflected light of the first wavelength to generate a plurality of first image frames and capturing reflected light of the second wavelength to generate a plurality of second image frames (Step $S_{12}$); dividing each of the first image frames and second image frames into at least two parts and calculating an average brightness of each part (Step $S_{13}$); using independent component analysis or blind source separation to analyze the average brightness of the each part of the first image frames to obtain a first intensity variation and to analyze the average brightness of the each part of the second image frames to obtain a second intensity variation (Step $S_{14}$); and calculating a physiological characteristic according to the first intensity variation and the second intensity variation (Step $S_{15}$). Details of every step have been described above and thus are not repeated herein.

Figure 8:
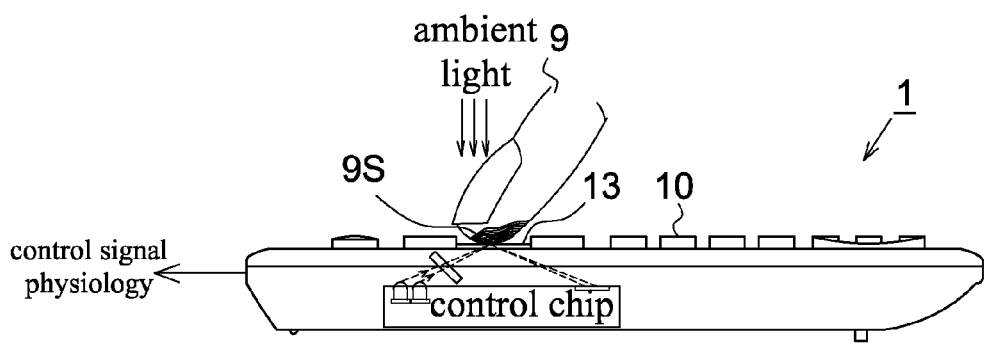
FIG. 8 shows a schematic diagram of the remote controller according to an alternative embodiment of the present disclosure.

In another embodiment, a part of or all of the light sources 111-112, the image sensor 14, the processing unit 15, the light control unit 16, the memory unit 17 and the transmission interface 18 may be manufactured as a control chip or a package as shown in FIG. 8. The control chip is configured to detect an operating state of the press buttons 10 and to detect the contact status, displacement and physiological characteristic of the finger 9, and to output encoded, sequenced and/or compressed contact status, displacement, physiological characteristic and control signal (said encoding process, sequential process and/or compression process may be performed by the transmission interface or by an additional communication unit), wherein the methods of calculating the contact status, displacement and physiological characteristic have been described above and thus details thereof are not repeated herein. In other words, the optical finger mouse and a control unit of the remote controller may be packaged as a control chip or a package. It is appreciated that the disposition of every element of the remote controller 1 shown in FIG. 8 is only exemplary and not to limit the present disclosure. In other embodiments, said compression process may be performed by an additional compression unit.

As mentioned above, the conventional remote controller can not detect the physiological characteristic of a user and the method of calculating the blood oxygenation for pulse oximeters cannot be applied to a remote controller since it can not detect a moving object. Therefore, the present disclosure further provides a remote controller (FIGS. 2B and 8) and a display system (FIG. 2A) that can detect both the finger information and the image control information, and control a display device to update images to be displayed according to the image control information and to display the finger information. The remote controller in the embodiments of the present disclosure may detect a finger displacement and a physiological characteristic of a user simultaneously and may eliminate the signal noise caused by finger movement and the interference from ambient light sources, and further has the mechanisms of entering sleep mode and removing invalid physiology information.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A remote controller configured to detect and output a displacement of a finger of a user, a physiological characteristic of the user and a control signal, the remote controller comprising:
a plurality of press buttons configured to trigger the control signal;

a first light source configured to provide light of a first wavelength to the finger;

a second light source configured to provide light of a second wavelength to the finger;

a light control unit configured to control on-states of the first light source and the second light source;

at least one image sensor configured to receive reflected light from the finger at a sampling frequency to generate a plurality of first image frames corresponding to the on-states of the first light source and a plurality of second image frames corresponding to the on-states of the second light source; and a processing unit configured to calculate both of the physiological characteristic and the displacement of the finger for controlling a cursor according to the first image frames and the second image frames captured by the at least one image sensor, and generate the control signal according to an operating state of the press buttons, wherein in calculating the physiological characteristic, the processing unit is configured to divide each of the first image frames into at least two parts and calculate an average brightness of each part, analyze the average brightness of the each part of the first image frames to obtain a first intensity variation, divide each of the second image frames into at least two parts and calculate an average brightness of each part, analyze the average brightness of the each part of the second image frames to obtain a second intensity variation, and calculate the physiological characteristic according to the first intensity variation and the second intensity variation.

2. The remote controller as claimed in claim 1, wherein the processing unit is further configured to calculate a heart rate according to a comparison of at least one pulse threshold with at least one of the first intensity variation and the second intensity variation.

3. The remote controller as claimed in claim 1, wherein the physiological characteristic comprises a blood oxygenation and a heart rate.

4. The remote controller as claimed in claim 1, wherein the processing unit is further configured to compare a brightness value of the first image frames and the second image frames with at least one brightness threshold to identify a contact status of the finger with the remote controller.

5. The remote controller as claimed in claim 1, wherein the processing unit is configured to calculate the displacement according to two of the first image frames, according to one of the first image frames and one of the second image frames, or according to two of the second image frames.

6. The remote controller as claimed in claim 1, wherein the light control unit is configured to alternatively enable the on-states of the first light source and the second light source such that the image sensor receives the reflected light associated with the first light source and the second light source alternatively; or the light control unit is configured to simultaneously enable the on-states of the first light source and the second light source such that the image sensor receives the reflected light associated with the first light source and the second light source simultaneously, and the image sensor comprises an optical filter covering at least a part of a sensing surface thereof.

7. The remote controller as claimed in claim 1, wherein the first light source, the second light source, the light control unit, the at least one image sensor and the processing unit are packaged as a control chip to output the physiological characteristic and the control signal processed by at least one of an encoding process, a sequential process and a compressing process.

8. The remote controller as claimed in claim 1, further comprising a touch member for the finger to operate thereon, wherein the touch member is one of the press buttons or separated from the press buttons.

9. The remote controller as claimed in claim 8, wherein the first light source and the second light source are configured to provide the light toward the touch member.

10. A remote controller for being operated by a user, the remote controller comprising:

a plurality of press buttons configured to trigger a control signal;

an optical finger mouse configured to detect both of a physiological characteristic of the user and a finger displacement of a finger of the user for controlling a cursor according to image frames captured by at least one image sensor, the optical finger mouse comprising:

a first light source configured to provide light of a first wavelength to the finger of the user;

a second light source configured to provide light of a second wavelength to the finger;

the at least one image sensor configured to receive reflected light from the finger to generate a plurality of first image frames corresponding to on-states of the first light source and a plurality of second image frames corresponding to on-states of the second light source; and a processing unit configured to divide each of the first image frames into at least two parts and calculate an average brightness of each part, analyze the average brightness of the each part of the first image frames to obtain a first intensity variation, divide each of the second image frames into at least two parts and calculate an average brightness of each part, analyze the average brightness of the each part of the second image frames to obtain a second intensity variation, and calculate the physiological characteristic according to the first intensity variation and the second intensity variation; and a transmission interface configured to output the control signal, the physiological characteristic and the finger displacement.

11. The remote controller as claimed in claim 10, wherein the optical finger mouse further comprises:

a light control unit configured to control the on-states of the first light source and the second light source.

12. The remote controller as claimed in claim 10, wherein the processing unit is further configured to calculate a heart rate according to a comparison of at least one pulse threshold with at least one of the first intensity variation and the second intensity variation.

13. The remote controller as claimed in claim 10, wherein the processing unit is further configured to compare a brightness value of the first image frames and the second image frames with at least one brightness threshold to identify a contact status of the finger with the optical finger mouse.

14. The remote controller as claimed in claim 10, wherein the optical finger mouse further comprises a touch member combined with one of the press buttons, and the first light source and the second light source are configured to provide the light toward the touch member.

15. A display system, comprising:
- a display device configured to display images; and
- a remote controller configured to output a control signal and a physiological characteristic to the display device to control the display device to update the images being displayed according to the control signal and to display the physiological characteristic, the remote controller comprising:
  - a first light source configured to provide light of a first wavelength to a finger;
  - a second light source configured to provide light of a second wavelength to the finger;
  - a light control unit configured to control on-states of the first light source and the second light source;
  - at least one image sensor configured to receive reflected light from the finger to generate a plurality of first image frames corresponding to the on-states of the first light source and a plurality of second image frames corresponding to the on-states of the second light source; and
  - a processing unit configured to
    - (i) divide each of the first image frames into at least two parts and calculate an average brightness of each part, and analyze the average brightness of the each part of the first image frames to obtain a first intensity variation;
    - (ii) divide each of the second image frames into at least two parts and calculate an average brightness of each part, and analyze the average brightness of the each part of the second image frames to obtain a second intensity variation; and
    - (iii) calculate the physiological characteristic according to the first intensity variation and the second intensity variation.

16. The display system as claimed in claim 15, wherein the display device is configured to generate a warning state when the physiological characteristic exceeds a predetermined value.

17. The display system as claimed in claim 15, wherein the processing unit is further configured to generate the control signal according to an operating state of a plurality of press buttons.

18. The display system as claimed in claim 17, wherein the remote controller further comprises a touch member combined with one of the press buttons and the first light source and the second light source are configured to provide the light toward the touch member.

19. The display system as claimed in claim 15, wherein
- the processing unit is further configured to calculate a displacement according to two of the first image frames, according to one of the first image frames and one of the second image frames, and according to two of the second image frames; and
- the remote controller is further configured to output the displacement to the display device to accordingly control a cursor displayed by the display device.

20. The display system as claimed in claim 15, wherein the processing unit is further configured to calculate a heart rate according to a comparison of at least one pulse threshold with at least one of the first intensity variation and the second intensity variation.

* * * * *